(12) United States Patent
Nakahara et al.

(10) Patent No.: US 6,294,190 B1
(45) Date of Patent: Sep. 25, 2001

(54) ANTIOBESTIC AGENT CONTAINING PROCYANIDIN AS THE ACTIVE INGREDIENT

(75) Inventors: Koichi Nakahara; Masaaki Nakai, both of Osaka; Yukiyoshi Tamura, Hiroshima-ken, all of (JP)

(73) Assignee: Suntory Limited (JP)

( * ) Notice: Subject to any disclaimer, the term of this patent is extended or adjusted under 35 U.S.C. 154(b) by 0 days.

(21) Appl. No.: 08/894,625
(22) PCT Filed: Dec. 26, 1996
(86) PCT No.: PCT/JP96/03810
 § 371 Date: Aug. 22, 1997
 § 102(e) Date: Aug. 22, 1997
(87) PCT Pub. No.: WO97/23210
 PCT Pub. Date: Jul. 3, 1997

(30) Foreign Application Priority Data
Dec. 26, 1995 (JP) .................................................. 7-338493

(51) Int. Cl.[7] ............................ A23K 1/165; A61K 47/00
(52) U.S. Cl. ........................... 424/442; 424/422; 424/439
(58) Field of Search ................................. 424/422, 439, 424/442

(56) References Cited
U.S. PATENT DOCUMENTS
4,166,861   9/1979   Bonati et al. .

(List continued on next page.)

FOREIGN PATENT DOCUMENTS
071307060A2   5/1996   (EP) .

(List continued on next page.)

OTHER PUBLICATIONS
Tsuda, et al., Antioxidative Components Isolated from the Seed of Tamarind, J. of Agri & Food Chem, Dec.–01–94, pp. 2671–2674.

(List continued on next page.)

*Primary Examiner*—Shelley A. Dodson

(74) *Attorney, Agent, or Firm*—Manelli Denison & Selter; Paul E. White, Jr.

(57) ABSTRACT

An antiobestic agent of the present invention having antiobestic effect, carbohydrase inhibitory effect, blood sugar increase inhibitory effect, monosaccharide absorption inhibitory effect, cholic acid adsorptive excretion promoting effect, cholesterol lowering effect, blood triglyceride lowering effect and lipase inhibitory effect and being useful not only as an antiobestic agent but also as an antilipotrophic agent, an antihyperlipemic agent, an antiarteriosclerotic agent and an antidiabetic agent. Tamarind seed coat extract containing a large amount of procyanidin, which is a trimer represented by the following formula and serves as the active ingredient in the present invention, exhibits a potent antiobestic effect as such without the need for further purification. The antiobestic agent of the present invention is usable as a carbohydrase inhibitor, a blood sugar increase inhibitor, a monosaccharide absorption inhibitor, a cholic acid adsorptive excretion promoter, a cholesterol lowering agent, a blood triglyceride lowering agent and a lipase inhibitor. Moreover, use of the antiobestic agent makes it possible to produce foods or beverages and animal feeds having these effects, thus contributing to the relief or prevention of diabetes and obesity in our daily life

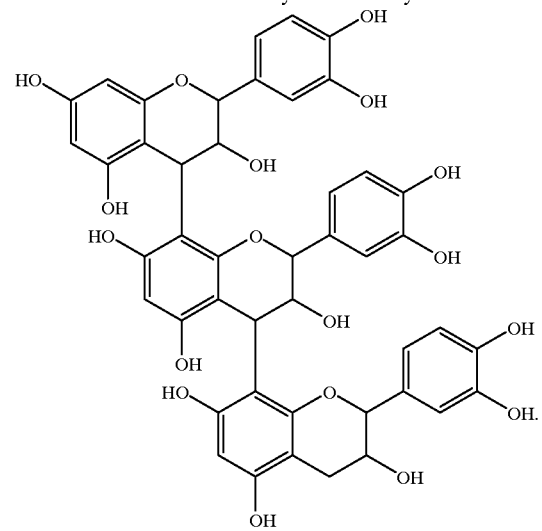

12 Claims, 4 Drawing Sheets

U.S. PATENT DOCUMENTS

| | | |
|---|---|---|
| 4,698,360 | 10/1987 | Masquelier . |
| 4,797,421 * | 1/1989 | Ariga et al. .................... 514/844 |
| 5,607,965 * | 3/1997 | Kondo et al. .................. 514/456 |

FOREIGN PATENT DOCUMENTS

| | | |
|---|---|---|
| 3-7232 | 1/1961 | (JP) . |
| WO 95/30427 | 11/1995 | (WO) . |

OTHER PUBLICATIONS

Sergio, W., A Natural Food, the Malabar Tamarind, May be Effective in the Treatment of Obesity, Medical Hypotheses, Sep.–1998, pp. 39–40.

"Yakuri to Chiryo" (Japanese Pharmacology and Therapeutics) vol. 19, No. 10, (Oct. 1991) p. 284.

"Sai–shin Igaku Dai–jiten (The New Medical Dictionary)" Ishiyaku–Shuppan, p. 1019 (1987).

Research in Experimental Medicine, vol. 175, 87 (1979.

Nippon Nogeikagaku Kaisha (Journal of the Agricultural Chemical Society of Japan), vol. 63, No. 2, p. 217 (1989.

New Current, vol. 6, No. 15, p. 2 (1995).

"Taisha (Metabolism)", vol. 24, No. 8, pp. 685–692 (1987).

Journal of Agricultural and Food Chemistry, vol. 24, No. 1, pp. 317–320 (1976).

J. Agr. Chem., vol. 69, p. 339 (1995).

* cited by examiner

* : Statistically significant difference from the control at $p<0.01$ by Student's $t$-test

* * * : Statistically significant difference from the control at $p<0.001$ by Student's $t$-test

** : Statiscally significant difference from the control at $p<0.005$ by Student's $t$-test

*** : Statiscally significant difference from the control at $p<0.001$ by Student's $t$-test

* : Statiscally significant difference from the control at $p<0.01$ by Student's $t$-test

** : Statiscally significant difference from the control at $p<0.005$ by Student's $t$-test

*: Statistically significant difference from the control at $p<0.01$ by Student's $t$-test

ANTIOBESTIC AGENT CONTAINING PROCYANIDIN AS THE ACTIVE INGREDIENT

This application is the national phase of international application PCT/JP96/-3810, filed Dec. 26, 1996 which was designated the U.S.

TECHNICAL FIELD

This invention relates to an antiobestic agent containing as the active ingredient tamarind seed coat extract (procyanidin).

BACKGROUND ART

With the recent tendency toward westernized eating habits, obesity caused by hypernutrition, etc. continues to increase. Similarly, there is observed a continuous increase in obese pet animals. Namely, there arises a serious problem of obesity which is one of the risk factors for arteriosclerosis and relates also to diabetes and hypertension. Obesity means a state where fat is excessively accumulated in the body. The accumulation of fat in the body is caused by the excessive intake of saccharide (carbohydrates) or fat.

The mechanism of obesity caused by the excessive intake of carbohydrates is as follows. Carbohydrates contained in foods or beverages are digested into mono-saccharides and absorbed into the body through the small intestine. The blood sugar level thus elevated induces the secretion of insulin which acts on fat cells. As a result, the monosaccharides in the blood are incorporated into the fat cells and converted into fat.

On the other hand, fat (triglycerides) with the highest caloric content among food components is digested by pancreatic lipase and absorbed through the small intestine. Excessive calory intake brings about an increase in reserve calories. That is, the excessive fat intake results in an increase in reserve calories and, in turn, obesity.

Accordingly, studies have been made on various anti-obestic agents for inhibiting some of these pathways toward obesity to thereby achieve an antiobestic effect. Namely, it is assumed that obesity can be prevented or relieved by the carbohydrase inhibitory effect, blood sugar increase inhibitory effect or monosaccharide absorption inhibitory effect, by which the pathway from the excessive intake of carbohydrates to obesity can be inhibited, or the cholic acid adsorptive excretion promoting effect, cholesterol lowering effect, blood triglyceride lowering effect or lipase inhibitory effect by which the pathway from the excessive intake of fat to obesity can be inhibited. Thus a number of studies have been carried out on drug ingredients having these effects.

First, illustration will be made of the carbohydrase inhibitory effect, monosaccharide absorption inhibitory effect and blood sugar increase inhibitory effect by which the pathway of the excessive intake of carbohydrates to obesity can be inhibited.

The term "carbohydrase" as used herein means digestive enzymes capable of degrading disaccharides (sucrose, maltose, isomaltose, lactose, trehalose, etc.) into monosaccharides (glucose, galactose, etc.) and involves α-glucosidase, β-glucosidase, sucrase, maltase, isomaltase, lactase, trehalase, etc. Carbohydrase inhibitors inhibit carbohydrases capable of degrading disaccharides into monosaccharides and thus retard the digestion of orally taken carbohydrates. As a result, a rapid increase in blood sugar level after a meal is retarded. As digestion is inhibited, disaccharides are slowly degraded into monosaccharides and the absorption of the monosaccharides into the intestinal tract is retarded. Then the increase in the blood sugar is suppressed. As a result, it is assumed that the synthesis of fat from carbohydrates is suppressed and the accumu-lation of somatic fat is thus inhibited.

It is considered that a rapid increase in blood sugar level after a meal due to the excessive intake of carbohydrates (saccharides) and excessive insulin secretion caused thereby will accelerate not only obesity but also diabetes or hyperlipemia [Yakuri to Chiryo (Pharmacology and Therapy), vol. 19, NO. 10 Oct. 284 (1991)]. It is therefore assumed that diabetes or hyperlipemia can be prevented or relieved by inhibiting carbohydrases. Moreover, the prevention of hyperlipemia is an efficacious methods for preventing arteriosclerosis [Saishin Igaku Daijiten (The Newest Medical Dictionary), Ishiyaku-Shuppan, K.K., 1019 (1987)].

Accordingly, carbohydrase inhibitors, mono-saccharide absorption inhibitors or blood sugar increase inhibitors are seemingly useful as antidiabetic agents, antihyperlipemic agents or antiarteriosclerotic agents.

Carbohydrase inhibitors commercially available at the present time include Acarbose (manufactured by Bayer AG) which is an a-glucosidase inhibitor and Voglibose (manufactured by Takeda Chemical Industries, Ltd.) which is a drug for ameliorating abnormally elevated blood sugar levels arising after a meal. As a results of animal and clinical tests, it is confirmed that these drugs inhibit an increase in blood sugar level after a meal. Also, it is reported that they are efficacious against obesity and diabetes [Res. Exp. Med., vol. 175, 87 (1979); J. Japan. Agr. Chem., vol. 63, 217 (1989); and New Current, vol. 6, 2 (1995)].

Next, the cholic acid adsorptive excretion promoting effect, cholesterol lowering effect, blood triglyceride lowering effect and lipase inhibitory effect will be illustrated. These effects inhibit the pathway from fat (triglyceride) intake to obesity.

Fat (triglycerides) is degraded by pancreatic lipase and absorbed through the small intestine. It is, therefore, estimated that the inhibition of lipase results in a decrease in the blood triglyceride level and, in its turn, contributes to the prevention of obesity. By suppressing the absorption of fat through the intestinal tract, furthermore, the serum lipid level can be lowered and thus hyperlipemia can be prevented.

A cholic acid (bile acid) adsorptive excretion promoter would bind to cholic acid in the intestinal tract and increase the excretion into the feces, thus inhibiting the exogenous cholesterol absorption. To compensate for the decrease in cholic acid due to the increase in the excreted cholic acid, the catabolism of cholesterol into cholic acid is accelerated in the liver. It is estimated that the blood cholesterol level is lowered thereby. That is to say, it is considered that a cholic acid adsorptive excretion promoter is useful as an antiobestic agent, since it accelerates the catabolism of cholesterol into cholic acid and, as a result, the cholesterol is consumed and the degradation of fat, which supplies cholesterol, is promoted.

As a drug having a cholic acid adsorptive excretion promoting effect, colestyramine which is a remedy for hypercholesterolemia may be cited. It is an anion exchange resin. When orally administered, this anion exchange resin adsorbs and fixes cholic acid under enterohepatic circulation in the intestine and thus inhibits the reabsorption of cholic acid. Then the conversion of cholesterol into cholic acid is accelerated in the liver and, as a result, the blood cholesterol level is lowered. However, colestyramine should be taken in a large dose (for example, 9 g of colestyramine suspended in 100 ml of water). In addition, it has another problem that the resine has a coarse and unpleasant texture remained in the mouth, which makes ingestion unpleasant.

As discussed above, there have been reported a number of chemically synthesized compounds each having characteristic effect(s) and some of them have been already put into practical use as drugs. However, these drugs suffer from some problems such as the necessity of being administered a large dose or having an unpleasant constitution upon administration. Since these compounds are chemically synthesized, moreover, the administration thereof is sometimes accompanied by anxiety about safety. Although it is desired to add antiobestic agents to foods or beverages so as to prevent obesity, the synthetic nature of such compounds and the large dose thereof make it impossible to realize this desire. Namely, it has been desired to develop a safe antiobestic agent having a natural origin so as to satisfy the above-mentioned.

In recent years, it has been clarified that some natural substances originating in plants (for example, bark of Morus alba or hydroxycitric acid which is a component of garcinia) have blood sugar increase inhibitory effect or antiobestic activity. However, it is not appropriate to add, for example, nojirimycin which is the active ingredient of bark of Morus alba to foods or beverages, since it has an excessively strong activity. It is also reported that guava leaf extract shows inhibitory effects on maltase and sucrase [J. Japan Agr. Chem., vol. 69, 339 (1995)]. However, this substance is satisfactory neither in blood sugar increase inhibitory effect nor antiobestic activity and thus no antiobestic agent has been developed so far with the use of the same. Disclosure of the Invention An object of the present invention is to provide a safe antiobestic agent comprising a substance originating in a natural material and having carbohydrase inhibitory effect, blood sugar increase inhibitory effect, monosaccharide absorption inhibitory effect, cholic acid adsorptive excretion promoting effect, cholesterol lowering effect, blood triglyceride lowering effect and lipase inhibitory effect.

The present inventors have conducted extensive studies to find a substance having antiobestic effect, i.e., carbohydrase inhibitory effect, blood sugar increase inhibitory effect, monosaccharide absorption inhibitory effect, cholic acid adsorptive excretion promoting effect, cholesterol lowering effect, blood triglyceride lowering effect and lipase inhibitory effect while exhibiting no harmful effect on the human body. As a result, they have found that a substance having a highly efficacious antiobestic effect is contained in tamarind seed coat extract, thus completing the present invention.

DETAILED DESCRIPTION OF THE INVENTION

Figure 1:
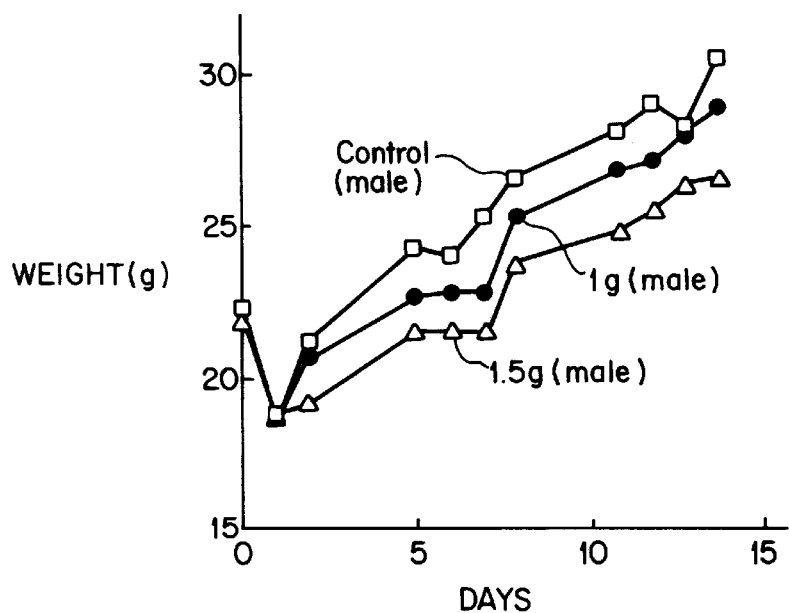
FIG. 1 is a graph which shows the antiobestic effect observed in an animal experiment with the use of the tamarind seed coat extract of the present invention.

The tamarind seed coat to be used in the present invention is the coat (husk) of tamarind (Tamarindus indica L.) seeds. The tamarind fruit is a dark purple, somewhat arched rod-shaped pod fruit of 7 to 20 cm in length and about 1.5 cm in width. The fruit shell is thin and fragile and a soft dark sarcocarp is contained therein. A dark and glossy seed, which is in the form of a flat quadrilateral of about 1 to 1.5 cm in length and about 4 mm in thickness, is enclosed in the sarcocarp. Tamarind sarcocarp has a sweet and sour taste and can be taken raw. Also, it may be added to foods as a spice. Alternatively, the sarcocarp is processed into a puree and, after adding spices, served as a chutney with curry. Also, the puree is dissolved in water and, after adding sugar, taken as a beverage. The seed has albumen which contains polysaccharides in the form of cell aggregates of about 40 to 80 $\mu$m in size. This albumen is widely employed in the production of foods as tamarind gum or tamarind seed gum which can be used as a thickening agent, gelatinizing agent, or pasting agent. The tamarind seed coat to be used in the present invention is a by-product obtained in the production of the tamarind gum. As it has no use save for the extraction of edible colorants, tamarind seed coat has been discarded hitherto.

Tamarind has been traditionally used as a natural medicine, namely, tamarind sarcocarp has been used as an anti-scorbutic agent, an antipyretic agent, an analgesic agent, an anti-rheumatic agent, a remedy for hemorrhoids, etc.; tamarind seed has been used as a remedy for dysentery; while tamarind flower and leaf have been used as a bathing preparation, etc. However, tamarind seed coat has never been employed hitherto as an antiobestic agent, a carbohydrase inhibitor, a blood sugar increase inhibitor, a monosaccharide absorption inhibitor, a cholic acid adsorptive excretion promoter, a cholesterol lowering agent, a blood triglyceride lowering agent or a lipase inhibitor.

The tamarind seed coat extract to be used in the present invention can be obtained by extracting tamarind seed coat with one or more solvents selected from among water, methanol, ethanol, isopropanol, butanol, propylene glycol, butylene glycol, glycerol, acetone, ethyl acetate and methyl ethyl ketone. When the tamarind seed coat extract is to be applied to foods, beverages or drugs, it is preferable to use water or a mixture of water with ethanol as the solvent from the viewpoint of the safety with the respect to the residual solvent. By taking the extraction efficiency into consideration, it is preferable that the content of organic solvent(s) in a solvent mixture with water is less than 90% by volume. In the extraction step, the ratio of tamarind seed coat to the solvent is not particularly restricted. However, it is preferable that the solvent is used in an amount of 2 to 1,000 parts by weight per part by weight of the tamarind seed coat, still preferably from 5 to 100 parts by weight from the viewpoint of the extracting operation and efficiency.

It is convenient in the operation that the extraction temperature falls within the range of room temperature to the boiling point of the solvent under atmospheric pressure. The extraction time is from several seconds to 2 days, preferably from 30 minutes to 24 hours, though it varies depending on the extraction temperature.

Although the tamarind seed coat may be extracted as such, it is preferable from the viewpoint of extraction efficiency to preliminarily grind the seed coat in a conventional manner.

The tamarind seed coat extract to be used in the present invention may be in any form. Namely, use can be made therefor of the tamarind seed coat extract thus obtained or a dry product obtained by filtering or centrifuging the extract so as to separate the solid matters, eliminating the solvent therefrom and, if necessary, drying. When the storage qualities and safety of organic solvents are taken into consideration, it is preferable to use a dry product.

As a result of extensive studies, the present inventors have found that procyanidin is the active ingredient of the tamarind seed coat extract exhibiting the antiobestic effect as well as the carbohydrase inhibitory effect, blood sugar increase inhibitory effect, monosaccharide absorption inhibitory effect, cholic acid adsorptive excretion promoting effect, cholesterol lowering effect, blood triglyceride lowering effect and lipase inhibitory effect.

Procyanidin is one of proanthocyanidins which mean condensed tannins occurring in various plants, i.e., a group of compounds formed by the condensation or polymerization of flavan-3-ol or flavan-3,4-diol serving as the constituting unit. Proanthocyanidins involve procyanidin, prodelphinidin, propelargonidin, proguibourtinidin, profisetinidin, prorobinetinidin, proteracacidin, promelacacidin, proapigeninidin, proluteolinidin and all of the stereoisomers thereof. The procyanidin of the present invention is a polymer having a chemical structure represented by the following formula I and a degree of polymerization of 2 to 80. The formula I shows a trimer.

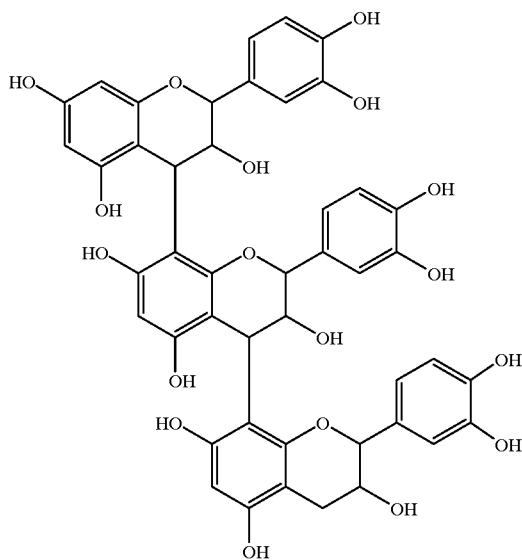

(I)

Examples of plants containing procyanidin other than tamarind seed coat include grape pericarp, grape seed, horse chestnut bark, cider and oolong stem tea.

When determined by the quantitive analysis of vanillin/hydrochloric acid method [J. Agric. Food Chem., 24, pp 317–320 (1976)], tamarind seed coat extract contains 85% procyanidin. When three marketed tamarind gum products, each of which is sold by San-EiGen F.F.I. Inc., are subjected to the determination by the same method, on the other hand, none of them contains procyanidin. Namely, the tamarind seed coat extract contains procyanidin in a high ratio not observed in any other plants. Regarding other plants, for example, JP Hei 3-7232-B states that a procyanidin dimer is obtained from horse chestnut bark. In this case, however, only 0.96 g of procyanidin is obtained from 1 kg of horse chestnut bark (yield: 0.096%). Even from a crude phenol-extract of horse chestnut bark, procyanidin can be obtained at only a low yield of 4.8%. Similarly, procyanidin can be obtained from cider. However, 120 mg of a procyanidin tetramer is obtained from 1 l of cider. From a crude polyphenol fraction (3.6 g) of cider, procyanidin is obtained at a yield of 3.3%.

Since tamarind seed coat extract contains procyanidin in a very large amount as described above, it is not necessary to further purify or fractionate the extract in order to employ the active ingredient procyanidin. Namely, the tamarind seed coat extract is usable as it is.

When it is desired to obtain further purified procyanidin, it is possible to purify the tamarind seed coat extract with the use of a synthetic adsorbent such as Diaion HP-20 or a gel filtration resin such as Sephadex LH-20.

As the antiobestic agent, carbohydrase inhibitor, blood sugar increase inhibitor, monosaccharide absorption inhibitor, cholic acid adsorptive excretion promoter, cholesterol lowering agent, blood triglyceride lowering agent and lipase inhibitor of the present invention, use can be made of preparations obtained by using the above-mentioned tamarind seed coat extract or procyanidin as the active ingredient optionally together with arbitrary adjuvants, fillers, water or organic solvents for preparing solutions, etc. In the case of oral administration, the antiobestic agent, carbohydrase inhibitor, blood sugar increase inhibitor, monosaccharide absorption inhibitor, cholic acid adsorptive excretion promoter, cholesterol lowering agent, blood triglyceride lowering agent or lipase inhibitor of the present invention may be given in a daily dose of from 1 to 300 mg/kg body weight (in terms of the tamarind seed coat extract), though the dose varies depending on the purpose of the administration and the conditions (sex, age, body weight, degree of obesity, general state of health, etc.) of the patient. The administration in a dose exceeding 300 mg/kg body weight causes no problem.

In Southeast Asia, tamarind fruit has been generally used as a spice from ancient times. On the other hand, its seed albumen has been employed as tamarind gum which has been generally used in the production of foods while its seed coat has been employed as an edible colorant. Accordingly, the tamarind seed coat extract to be used in the present invention involves no problem as regards safety.

When the antiobestic agent, carbohydrase inhibitor, blood sugar increase inhibitor, monosaccharide absorption inhibitor, cholic acid adsorptive excretion promoter, cholesterol lowering agent, blood triglyceride lowering agent and lipase inhibitor of the present invention containing the tamarind seed coat extract obtained above or procyanidin as the active ingredient are used as drugs, they may be processed into preparations for oral administration, for example, dusts, granules, tablets, capsules, pills, troches, solutions for internal use, suspensions, emulsions and syrups. These products may be employed either alone or in combination depending on the symptoms. These preparations can be produced by blending the principal agent with known carriers commonly employed in the field of pharmaceutical manufacturing such as fillers, binders, preservatives, antioxidants, disintegrators, lubricating agents or corrigents in a conventional manner. In the production of the drugs of the present invention, it is also possible to add one or more plant extracts having antiobestic effect such as laurel, guava leaves, wheat, oolong tea, garcinia and Gymnema sylvestre.

The tamarind seed coat extract or procyanidin is soluble in water and easily gives a uniform solution at a practically usable concentration. Thus, it can be added to aqueous drugs without any difficulty.

As carriers, use can be made of standard ones depending on the dosage form without particular restriction. Preferable examples thereof include solid carriers such as starch, lactose, mannitol, carboxymethylcellulose, corn starch and inorganic salts; liquid carriers such as distilled water, physiological saline, aqueous solution of glucose, alcohols such as ethanol, propylene glycol and polyethylene glycol; and oily carriers such as various animal and vegetable oils, white vaseline, paraffin and wax.

The foods or beverages of the present invention can be prepared by adding the antiobestic agent, carbohydrase inhibitor, blood sugar increase inhibitor, monosaccharide absorption inhibitor, cholic acid adsorptive excretion promoter, cholesterol lowering agent, blood triglyceride lowering agent or lipase inhibitor of the present invention to foods or beverages either as such or after blending with various components commonly employed in foods. In the production of foods or beverages of the present invention, it is also possible to add one or more other plant extracts having antiobestic effect such as laurel, guava leaves, wheat, oolong tea, garcinia and *Gymnema sylvestre.*

The foods or beverages thus produced may be in any form such as solid foods, semi-fluid foods such as cream or jam, gelatinous foods or beverages. For example, it is possible to prepare capsules, granules, tablets or drinks. Furthermore, arbitrary bases commonly employed in the art may be used together therewith so as to give soft drinks, juice, coffee, tea, liquors, milk, milk serum drinks, yoghurt drinks, candies, chewing gums, chocolates, gum-drops, yoghurt, ice-creams, puddings, mizuyokan (soft jellied bean paste), etc. The tamarind seed coat extract or procyanidin is soluble in water and easily gives an uniform solution at a practically usable concentration. Thus, it can be added to aqueous foods without any difficulty.

The tamarind seed coat extract or procyanidin has a slight astringency. If this astringency gives rise to problems in the preparation of foods or beverages containing the antiobestic agent, carbohydrase inhibitor, blood sugar increase inhibitor, monosaccharide absorption inhibitor, cholic acid adsorptive excretion promoter, cholesterol lowering agent, blood triglyceride lowering agent or lipase inhibitor of the present invention, it can be masked by adding cyclodextrin, dextrin, lactose, sugar alcohols (for example, sorbitol, maltitol, xylitol or erythritol), etc. To foods or beverages, the tamarind seed coat extract is preferably added at a concentration of from 0.0001 to 10.0% by weight (in terms of dry matter), still preferably from 0.01 to 5.0% by weight, taking the astringency and the color tone into consideration.

To produce these foods or beverages, various components are usable depending on the type of the product. For example, use may be appropriately made of materials commonly employed in food manufacturing such as glucose, fructose, sucrose, maltose, sorbitol, stevios100de, rubusoside, corn syrup, lactose, citric acid, tartaric acid, malic acid, succinic acid, lactic acid, L-ascorbic acid, dl-a-tocopherol, sodium erythorbate, glycerol, propylene glycol, glycerol fatty acid esters, polyglycerine fatty acid esters, sucrose fatty acid esters, sorbitan fatty acid esters, propylene glycol fatty acid esters, acacia gum, carrageenan, casein, gelatin, pectin, agar, vitamin B group, nicotinic-acid amide, calcium pantothenate, amino acids, calcium salts, colorants, flavoring substances and preservatives.

The animal feeds of the present invention can be produced by appropriately blending the antiobestic agent, carbohydrase inhibitor, blood sugar increase inhibitor, monosaccharide absorption inhibitor, cholic acid adsorptive excretion promoter, cholesterol lowering agent, blood triglyceride lowering agent or lipase inhibitor of the present invention with various components commonly employed in animal feeds depending on the purpose. Examples of the animal feeds include livestock feeds and pet feeds such as cat foods, dog foods and rabbit foods.

In the production of the animal feeds of the present invention, it is also possible to add one or more other plant extracts having antiobestic effect such as laurel, guava leaves, wheat, oolong tea, garcinia and Gymnema sylvestre.

The tamarind seed coat extract or procyanidin has slight astringency. When this astringency causes some troubles in the preparation of animal feeds containing the antiobestic agent of the present invention, it can be masked by adding cyclodextrin, dextrin, lactose, sugar alcohols (for example, sorbitol, maltitol, xylitol or erythritol, etc.), etc. To animal feeds, the tamarind seed coat extract is preferably added at a concentration of from 0.0001 to 10.0% by weight (in terms of dry matter), still preferably from 0.01 to 5.0% by weight, by taking the astringency and the color tone into consideration.

The antiobestic agent, carbohydrase inhibitor, blood sugar increase inhibitor, monosaccharide absorption inhibitor, cholic acid adsorptive excretion promoter, cholesterol lowering agent, blood triglyceride lowering agent and lipase inhibitor of the present invention are also usable as additives for foods or beverages or animal feeds. In these additives, the antiobestic agent, carbohydrase inhibitor, blood sugar increase inhibitor, monosaccharide absorption inhibitor, cholic acid adsorptive excretion promoter, cholesterol lowering agent, blood triglyceride lowering agent and lipase inhibitor of the present invention may be employed, either as such or together with carriers commonly used in the production of foods or beverages or animal feeds, and processed into powders, granules, pastes, capsules, syrups, solids, gels, solutions, suspensions, emulsions, etc. These additives can be added to foods or beverages or animal feeds during the production of the same or after the completion of production so as to impart the antiobestic effect as well as the carbohydrase inhibitory effect, blood sugar increase inhibitory effect, monosaccharide absorption inhibitory effect, cholic acid adsorptive excretion promoting effect, cholesterol lowering effect, blood triglyceride lowering effect and lipase inhibitory effect thereto.

To further illustrate the present invention in greater detail, and not by way of limitation, the following Examples on the production of the tamarind seed coat extract, carbohydrase inhibition test, obesity inhibition test, blood sugar increase inhibition test, monosaccharide absorption inhibition test, cholic acid adsorptive excretion test, blood cholesterol lowering test, blood triglyceride lowering test, lipase inhibition test and the production of various drugs, foods or beverages and animal feeds will be given.

EXAMPLE 1

Production of Tamarind Seed Coat Extract (1):

100 g of ground tamarind seed coat was fed into a 3,000 ml Erlenmeyer flask and 1,000 ml of 50% ethanol was added thereto as the extraction solvent. After being allowed to stand at 40° C. for 24 hours to thereby extract the soluble components, the mixture was filtered and the filtrate thus obtained was evaporated to dryness under reduced pressure to thereby give 30.0 g of a solid product.

EXAMPLE 2
Production of Tamarind Seed Coat Extract (2):

100 g of ground tamarind seed coat was fed into a 3,000 ml Erlenmeyer flask and 1,000 ml of 50% acetone was added thereto as the extraction solvent. After allowing to stand at 40° C. for 24 hours to thereby extract the soluble components, the mixture was filtered and the filtrate thus obtained was evaporated to dryness under reduced pressure to thereby give 30.0 g of a solid product.

EXAMPLE 3
Production of Tamarind Seed Coat Extract (3):

100 g of ground tamarind seed coat was fed into a 3,000 ml Erlenmeyer flask and 1,000 ml of water was added thereto as the extraction solvent. After extracting the soluble components at 100° C. for 2 hours, the mixture was filtered and the filtrate thus obtained was evaporated to dryness under reduced pressure to thereby give 13.2 g of a solid product.

EXPERIMENTAL EXAMPLE 1
Determination of α-glucosidase Inhibitory Activity:

The α-glucosidase inhibitory activity of the tamarind seed coat extract obtained in Example 1 was determined by the following method with the use of α-glucosidase (manufactured by Toyobo Co., Ltd.) originating in a yeast. The enzymatic activity was measured by the colorimetric determination of the increase in the capability of reducing glucose and fructose formed by the hydrolysis of sucrose by using dinitrosalicylic acid. Table 1 shows the result.

| (Method for determining α-glucosidase-inhibitory activity) | |
| --- | --- |
| 50 mM sucrose solution (in 50 mM potassium phosphate buffer: pH 7.0) | 0.50 ml |
| α-glucosidase solution | 0.25 ml |
| aqueous solution of tamarind seed coat extract | 0.05 ml |
| 50 mM potassium phosphate buffer (pH 7.0) | 0.20 ml |

The above solutions were mixed together and the enzymatic reaction mixture thus obtained was introduced into a test tube and reacted at 37° C. for 30 minutes. To the reducing sugars thus formed was added 1 ml of dinitrosalicylic acid solution (1% of sodium hydroxide, 5% of potassium sodium tartrate, 0.2% of phenol, 1% of dinitrosalicylic acid, 0.05% of sodium sulfite). After reacting at 100° C. for 10 minutes, the absorbance of the reaction mixture was measured at 540 nm. In a control case, the sample solution was substituted by the above-mentioned potassium phosphate buffer. In each blank case, further, the enzyme solution was substituted by the above-mentioned potassium phosphate buffer. The inhibitory activity is expressed in the inhibitory rate calculated in accordance with the following formula. Similarly, the inhibitory activity of hot-water extract of guava leaves, i.e., a substance known as having an inhibitory activity on α-glucosidase originating in plants was determined.

Inhibitory rate (%)={(A−B)−(C−D)}/(A−B)×100 wherein

A: the absorbance of the control solution;
B: the absorbance of the blank of the control solution;
C: the absorbance of the sample solution; and
D: the absorbance of the blank of the sample solution.

On the basis of the data thus obtained, the concentration of the aqueous solution of the tamarind seed coat extract achieving an inhibitory rate of 50% ($IC_{50}$) was determined. A lower $IC_{50}$ represents a stronger enzyme inhibitory activity.

TABLE 1

| Sample | $IC_{50}$ (µg/ml) |
| --- | --- |
| tamarind seed coat extract | 1.3 |
| guava leaf (hot water-extract) | 20.0 |

EXPERIMENTAL EXAMPLE 2
Sucrase Inhibitory Activity Test:

The sucrase inhibitory activity of the tamarind seed coat extract obtained in Example 1 was determined by the following method with the use of sucrase originating in rat small intestine contained in rat small intestine acetone powder (manufactured by Sigma). The enzymatic activity was measured by the determination of the increase in the glucose formed by the hydrolysis of sucrose by using Glucose CII-Test Wako (manufactured by Wako Pure Chemical Industries, Ltd.), i.e. a kit for determining glucose. Table 2 shows the result.

| (Method for determining sucrase-inhibitory activity) | |
| --- | --- |
| 50 mM sucrose solution (in 50 mM potassium phosphate buffer: pH 7.0) | 0.50 ml |
| rat small intestine acetone powder solution | 0.25 ml |
| aqueous solution of tamarind seed coat extract | 0.05 ml |
| 50 mM potassium phosphate buffer (pH 7.0) | 0.20 ml |

The above solutions were mixed together and the enzymatic reaction mixture thus obtained was introduced into a test tube and reacted at 37° C. for 30 minutes. The glucose thus formed was determined by quantifying with Glucose CII-Test Wako (manufactured by Wako Pure Chemical Industries, Ltd.), i.e. a kit for determining glucose. In a control case, the sample solution was substituted by the above-mentioned potassium phosphate buffer. In each blank case, further, the enzyme solution was substituted by the above-mentioned potassium phosphate buffer. The inhibitory activity is expressed in the inhibitory rate calculated in accordance with the following formula. Similarly, the inhibitory activity of hot-water extract of guava leaves, i.e., a substance known as having an inhibitory activity on sucrease originating in plants was determined.

Inhibitory rate (%)={(A−B)−(C−D)}/(A−B)×100 wherein

A: the absorbance of the control solution;
B: the absorbance of the blank of the control solution;
C: the absorbance of the sample solution; and
D: the absorbance of the blank of the sample solution.

On the basis of the data thus obtained, the concentration of the aqueous solution of the tamarind seed coat extract achieving an inhibitory rate of 50% ($IC_{50}$) was determined. A lower $IC_{50}$ represents a stronger enzyme inhibitory activity.

TABLE 2

| Sample | $IC_{50}$ (µg/ml) |
| --- | --- |
| tamarind seed coat extract | 400 |
| guava leaf (hot water-extract) | 1000 |

EXPERIMENTAL EXAMPLE 3

Maltase Inhibitory Activity Test:

The maltase inhibitory activity of the tamarind seed coat extract obtained in Example 1 was determined by the following method with the use of maltase originating in rat small intestine contained in rat small intestine acetone powder (manufactured by Sigma). The enzymatic activity was measured by the determination of the increase in the glucose formed by the hydrolysis of maltose by using Glucose CII-Test Wako (manufactured by Wako Pure Chemical Industries, Ltd.), i.e. a kit for determining glucose. Table 3 shows the result.

| (Method for determining maltase-inhibitory activity) | |
| --- | --- |
| 50 mM maltose solution (in 50 mM potassium phosphate buffer: pH 7.0) | 0.50 ml |
| rat small intestine acetone powder solution | 0.25 ml |
| aqueous solution of tamarind seed coat extract | 0.05 ml |
| 50 mM potassium phosphate buffer (pH 7.0) | 0.20 ml |

The above solutions were mixed together and the enzymatic reaction mixture thus obtained was introduced into a test tube and reacted at 37° C. for 30 minutes. The glucose thus formed was determined with Glucose CII-Test Wako (manufactured by Wako Pure Chemical Industries, Ltd.), i.e. a kit for determining glucose. In a control case, the sample solution was substituted by the above-mentioned potassium phosphate buffer. In each blank case, further, the enzyme solution was substituted by the above-mentioned potassium phosphate buffer. The inhibitory activity is expressed in the inhibitory rate calculated in accordance with the following formula. Similarly, the inhibitory activity of hot-water extract of guava leaves, i.e., a substance known as having an inhibitory activity on maltase originating in plants was determined.

Inhibitory rate $(\%) = \{(A-B)-(C-D)\}/(A-B) \times 100$ wherein

A: the absorbance of the control solution;

B: the absorbance of the blank of the control solution;

C: the absorbance of the sample solution; and

D: the absorbance of the blank of the sample solution.

On the basis of the data thus obtained, the concentration of the aqueous solution of the tamarind seed coat extract achieving an inhibitory rate of 50% ($IC_{50}$) was determined. A lower $IC_{50}$ represents a stronger enzymer inhibitory activity.

TABLE 3

| Sample | $IC_{50}$ (µg/ml) |
| --- | --- |
| tamarind seed coat extract | 200 |
| guava leaf (hot water-extract) | 400 |

EXPERIMENTAL EXAMPLE 4

Obesity Inhibition Test:

By using the tamarind see coat extract obtained in Example 1, an obesity inhibition test was performed in the following manner. FIG. 1 shows the results.

(Method for Determining Obesity-inhibitory Activity)

Crj:ICR male mice (obtained from Charles River Japan Ltd) aged 7 weeks were preliminarily fed for 1 week, then classified into groups each having 7 animals and subjected to the test. The animals were fed in a thermo-hygrostat at a temperature of 23±1° C. and a humidity of 55±5% under illumination for 12 hours per day. They were fed with a feed Labo MR (manufactured by Nippon Nosan) and allowed to take water ad libitum. The test samples were in the form of suspensions in a 5% acacia gum. The concentration of each sample solution was regulated so that 0.1 ml of the solution was given per 10 g body weight of animal. The doses employed were 1.5 g/kg and 1 g/kg. To a control group, a 5% acacia gum solution was administered. After fasting the mice, the sample was administered once by force on the next day. During the test period over 2 weeks, the body weight and general conditions were monitored.

(Results)

1) Body weight: as FIG. 1 shows, the body weight gain was inhibited in each test group (tamarind seed coat extract administration), compared with the control group.

2) General conditions: each test group showed no abnormality compared with the control group, which means that the tamarind seed coat extract is free from any problem in safety.

EXPERIMENTAL EXAMPLE 5

Figure 2:
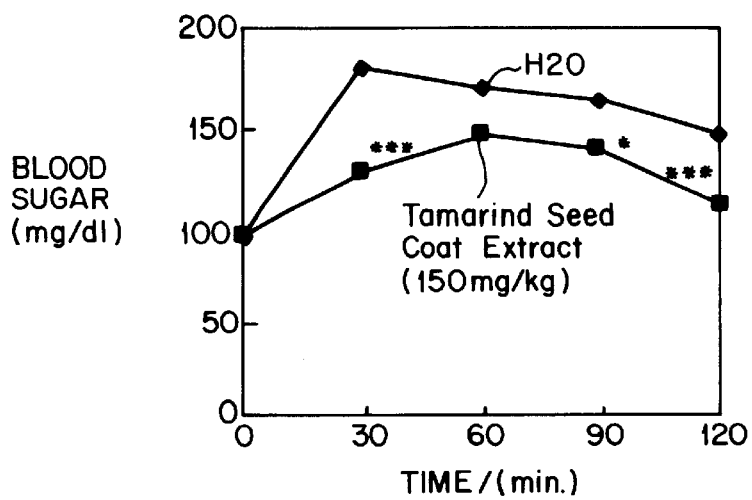
FIG. 2 is a graph which shows the blood sugar increase inhibitory effect observed in an animal experiment with the use of the tamarind seed coat extract of the present invention.

Blood Sugar Increase Inhibition Test (1):

By using the tamarind seed coat extract obtained in Example 1, a blood sugar increase inhibition test was performed in the following manner. FIG. 2 shows the results.

(Method for Determining Blood Sugar Increase Inhibitory Activity)

ddY male mice (obtained from Charles River Japan Ltd) aged 5 weeks were preliminarily fed for 1 week, then classified into groups each having 5 animals and subjected to the test. After fasting overnight, the fasting blood glucose level of each mouse was determined. Then the tamarind seed coat extract and sucrose were orally administered once by force. The concentration of the tamarind seed coat extract was regulated so that 0.1 ml thereof was given per 10 g body weight of animal. The dose employed were 150 mg/kg. To a control group, deionized water was administered. The concentration of sucrose was regulated so that 0.1 ml thereof was given per 10 g body weight of animal. The dose was 8 g/kg. After the administration, the blood sugar level was determined every 30 minutes.

(Results)

In the test group to which the tamarind seed coat extract had been administered, the increase in the blood sugar level was significantly inhibited, compared with the control group, from the point 30 minutes after sucrose-loading, as FIG. 2 shows. Also, the tamarind seed coat extract was effective in retarding the degradation and absorption of sucrose.

EXPERIMENTAL EXAMPLE 6

Figure 3:
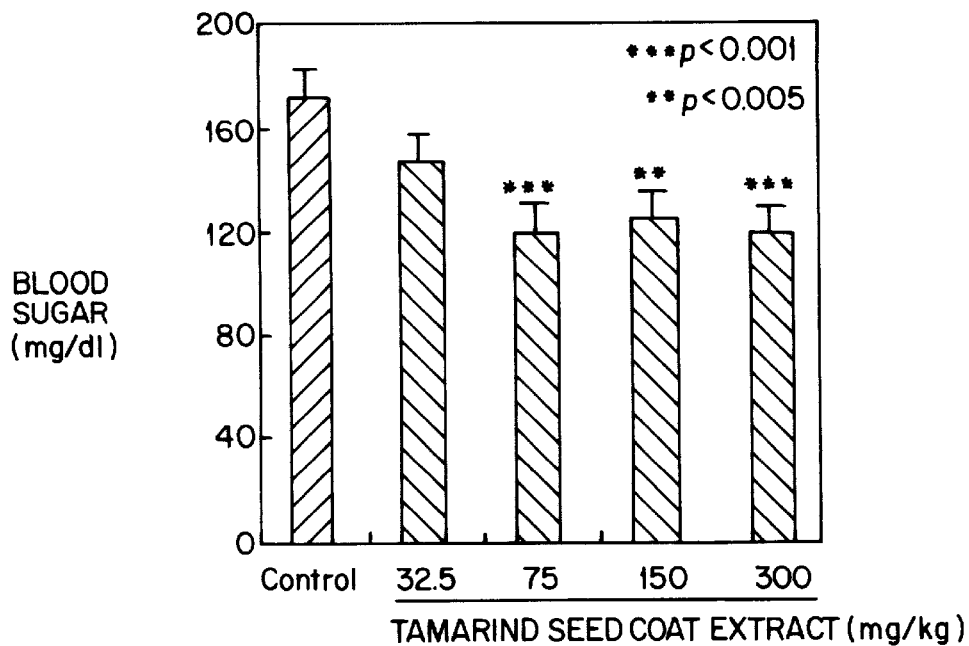
FIG. 3 is a graph which shows dose-dependency of the blood sugar increase inhibitory effect observed in an animal experiment with the use of the tamarind seed coat extract of the present invention.

Blood Sugar Increase Inhibition Test (2):

By using the tamarind seed coat extract obtained in Example 1, examination was made on the concentration-dependency and the effective dose in a blood sugar increase inhibition test. FIG. 3 shows the results. (Method for determining concentration-dependency of blood sugar increase inhibitory activity)

ddY male mice (obtained from Charles River Japan Ltd) aged 5 weeks were preliminarily fed for 1 week, then classified into groups each having 7 animals and subjected to the test. After fasting overnight, the fasting blood glucose level of each mouse was determined. Then the tamarind seed coat extract and sucrose were orally administered once by force. 30 minutes after the administration, the blood sugar level was determined. The concentration of the tamarind seed coat extract was regulated so that 0.1 ml thereof was given per 10 g body weight of animal. The doses employed were from 32.5 to 300 mg/kg. To a control group, deionized water was administered. The concentration of sucrose was regulated so that 0.1 ml thereof was given per 10 g body weight of animal. The dose was 8 g/kg.

(Results)

In the test groups to which the tamarind seed coat extract had been administered, the increase in the blood sugar level was inhibited depending on the concentration, compared with the control group, 30 minutes after sucrose-loading, as FIG. 3 shows. In this experiment with the use of mice, the blood sugar increase was significantly inhibited at 75 mg/kg or above, while a tendency toward inhibition was observed in the group of the dose of 32.5 mg/kg.

EXPERIMENTAL EXAMPLE 7

Figure 4:
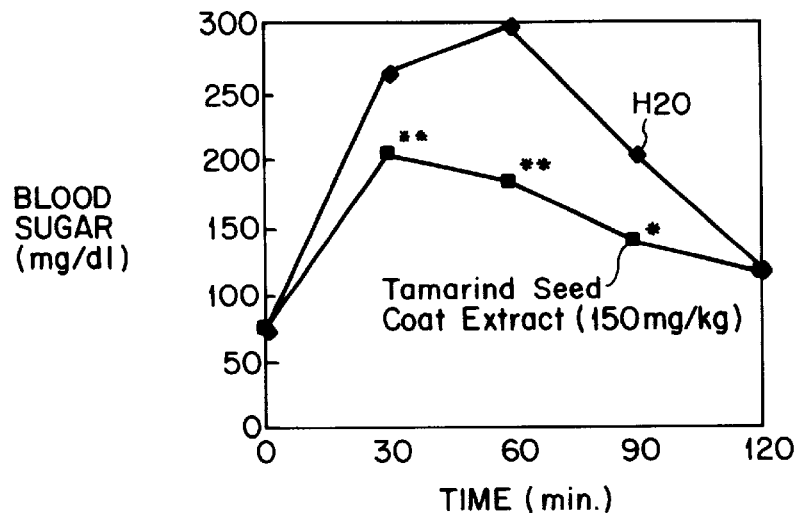
FIG. 4 is a graph which shows the monosaccharide absorption inhibitory effect observed in an animal experiment with the use of the tamarind seed coat extract of the present invention.

Monosaccharide Absorption Inhibition Test:

By using the tamarind seed coat extract obtained in Example 1, a monosaccharide absorption inhibition test was performed in the following manner. FIG. 4 shows the results.

(Method for Determining Monosaccharide Absorption Inhibitory Activity)

ICR female mice (obtained from Charles River Japan Ltd) aged 7 weeks were preliminarily fed for 1 week, then classified into groups each having 5 animals and subjected to the test. After fasting overnight, the fasting blood glucose level of each mouse was determined. Then the tamarind seed coat extract and monosaccharide (glucose) were orally administered once by force. The concentration of the tamarind seed coat extract was regulated so that 0.1 ml thereof was given per 10 g body weight of animal. The dose employed were 150 mg/kg. To a control group, deionized water was administered. The concentration of glucose was regulated so that 0.1 ml thereof was given per 10 g body weight of animal. The dose was 4 g/kg. After the administration, the blood sugar level was determined every 30 minutes.

(Results)

In the test group to which the tamarind seed coat extract had been administered, the increase in the blood sugar level was significantly inhibited, compared with the control group, from the point 30 minutes after glucose-loading, as FIG. 4 shows. Namely, the tamarind seed coat extract inhibited the absorption of glucose through the intestinal tract.

EXPERIMENTAL EXAMPLE 8

Figure 5:
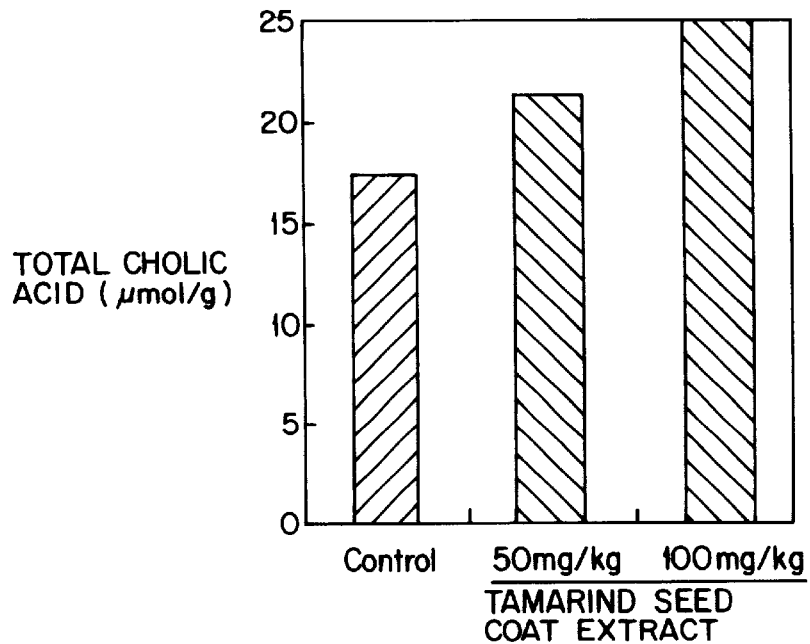
FIG. 5 is a graph which shows the cholic acid adsorptive excretion promoting effect observed in an animal experiment with the use of the tamarind seed coat extract of the present invention.

Cholic Acid Adsorptive Excretion Test:

By using the tamarind seed coat extract obtained in Example 1, a cholic acid adsorptive excretion test was performed in the following manner. FIG. 5 shows the results.

(Method for Determining Cholic Acid Adsorptive Excretion Promoting Activity)

ddY male mice (obtained from Charles River Japan Ltd) aged 7 weeks were preliminarily fed for 1 week, then classified into groups each having 15 animals and subjected to the test. The tamarind seed coat extract was orally administered to the mice by force continuously for 12 days. The concentration of the tamarind seed coat extract was regulated so that 0.1 ml thereof was given per 10 g body weight of animal. The doses employed were 50 and 100 mg/kg. To a control group, deionized water was administered. The animals were allowed to take feed and water ad libitum. The feces of each group was combined and the cholic acid excreted thereinto was determined by colorimetry with the use of Total Bile Acid Test Wako (manufactured by Wako Pure Chemical Industries, Ltd.), i.e, a kit for total bile acid determination.

(Results)

In the test groups to which the tamarind seed coat extract had been administered, the amount of the cholic acid excreted via adsorption increased depending on the concentration, compared with the control group, as FIG. 5 shows. Namely, the tamarind seed coat extract inhibited the re-absorption of cholic acid through the intestinal tract and promoted the excretion thereof.

EXPERIMENTAL EXAMPLE 9

Figure 6:
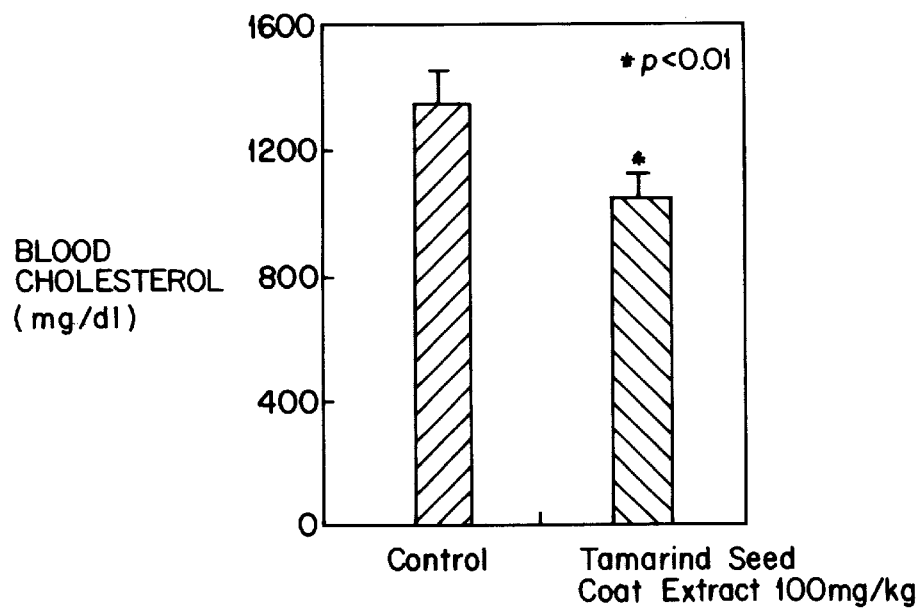
FIG. 6 is a graph which shows the blood cholesterol lowering effect observed in an animal experiment with the use of the tamarind seed coat extract of the present invention.

Blood Cholesterol Lowering Test:

By using the tamarind seed coat extract obtained in Example 1, a blood cholesterol lowering test was performed in the following manner. FIG. 6 shows the results.

(Method for Determining Blood Cholesterol Lowering Activity)

Wister female rats (obtained from Charles River Japan Ltd) aged 5 weeks were preliminarily fed for 1 week, then classified into groups each having 7 animals and subjected to the test. The tamarind seed coat extract was orally administered to the rats by force continuously for 14 days. The concentration of the tamarind seed coat extract was regulated so that 0.1 ml thereof was given per 10 g body weight of animal. The dose employed was 100 mg/kg. To a control group, deionized water was administered. During the test period, the animals were allowed to take a cholesterol-enriched feed and water ad libitum. On the final day of the test, the blood was collected and the blood cholesterol level was measured.

(Results)

In the test group to which the tamarind seed coat extract had been administered, the blood cholesterol level was significantly lowered, compared with the control group, as FIG. 6 shows.

EXPERIMENTAL EXAMPLE 10

Figure 7:
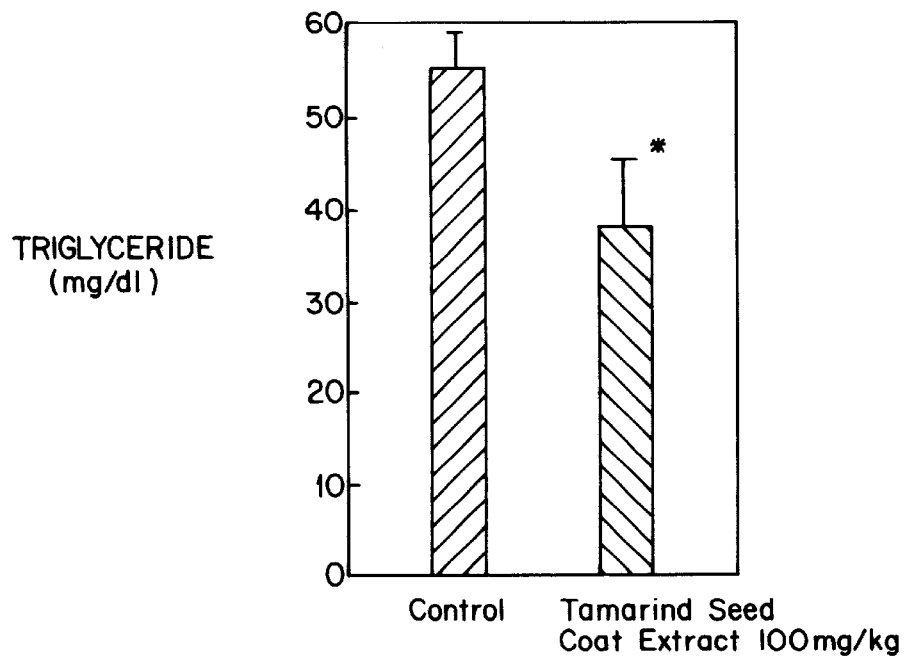
FIG. 7 is a graph which shows the blood triglyceride lowering effect observed in an animal experiment with the use of the tamarind seed coat extract of the present invention.

Blood Triglyceride Lowering Test:

By using the tamarind seed coat extract obtained in Example 1, a blood triglyceride lowering test was performed in the following manner. FIG. 7 shows the results.

(Method for Determining Blood Triglyceride Lowering Activity)

ddY male mice (obtained from Charles River Japan Ltd) aged 5 weeks were preliminarily fed for 1 week, then classified into groups each having 15 animals and subjected to the test. The tamarind seed coat extract was orally administered to the mice by force continuously for 14 days. The concentration of the tamarind seed coat extract was regulated so that 0.1 ml thereof was given per 10 g body weight of animal. The dose employed was 100 mg/kg. To a control group, deionized water was administered. The animals were allowed to take feed and water ad libitum. On the final day of the test, the blood was collected and the free triglycerides in the blood were determined.

(Results)

In the test group to which the tamarind seed coat extract had been administered, the blood triglyceride level was significantly lowered, compared with the control group, as FIG. 7 shows.

EXPERIMENTAL EXAMPLE 11

Figure 8:
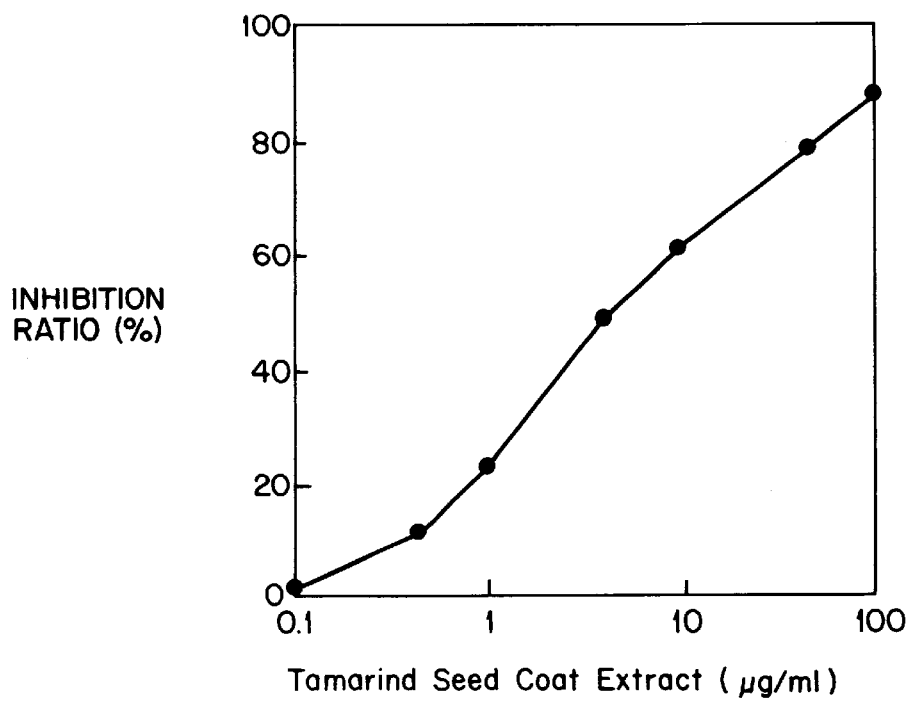
FIG. 8 is a graph which shows the lipase inhibitory effect with the use of the tamarind seed coat extract of the present invention.

Lipase Inhibition Test:

The lipase inhibitory activity of the tamarind seed coat extract obtained in Example 1 was determined by the following method with the use of swine pancreatic lipase (manufactured by Sigma). Table 4 and FIG. 8 show the results. The enzymatic activity was measured by the colorimetric determination of the increase in the dimercaprol formed by the hydrolysis of dimercaprol tributyrate, i.e., the substrate of lipase, by using 5'5-dithiobis-2-nitrobenzoic acid.

| (Method for determining lipase-inhibitory activity) | |
|---|---|
| 5'5-dithiobis-2-nitrobenzoic acid solution (in buffer: pH 7.5) | 1.00 ml |
| lipase solution (in buffer: pH 7.5) | 0.05 ml |
| aqueous solution of tamarind seed coat extract | 0.10 ml |
| dimercaprol tributyrate solution | 0.10 ml |

The above solutions were mixed together and the enzymatic reaction mixture thus obtained was introduced into a test tube and reacted at 30° C. for 30 minutes. At the completion of the reaction, 2.00 ml of an acidic anionic surfactant was added to thereby cease the reaction with lipase. The absorbance of the mixture at 412 nm was measured. In a control case, the sample solution was substituted by distilled water. In each blank case, further, the enzyme solution was substituted by the buffer. The inhibitory activity is expressed in the inhibitory rate calculated in accordance with the following formula.

$$\text{Inhibitory rate } (\%) = \{(A-B)-(C-D)\}/(A-B) \times 100$$

wherein

A: the absorbance of the control solution;

B: the absorbance of the blank of the control solution;

C: the absorbance of the sample solution; and

D: the absorbance of the blank of the sample solution.

On the basis of the data thus obtained, the concentration of the aqueous solution of the tamarind seed coat extract achieving an inhibitory rate of 50% ($IC_{50}$) was determined. A lower $IC_{50}$ represents a stronger enzyme inhibitory activity.

TABLE 4

| Sample | $IC_{50}$ (μg/ml) |
|---|---|
| tamarind seed coat extract | 8.0 |

EXAMPLE 4

Tablet:

Tablets were produced by using the tamarind seed coat extract of Example 1. Namely, 150 g of the tamarind seed coat extract of Example 1 was mixed with the same amount of lactose and 5 g of magnesium stearate. Then the obtained mixture was processed into tablets (diameter: 10 mm, weight: 300 mg) with a single-tabletting machine.

EXAMPLE 5

Granule:

The tablets obtained in the above Example 4 were ground, dressed and sieved to thereby give granules of 20–50 mesh.

EXAMPLE 6

Candy:

By using the tamarind seed coat extract of Example 1, candies of the following composition were produced. Although the tamarind seed coat extract was contained therein, these candies had a pleasant taste without any bitterness.

| (Component) | (Content %) |
|---|---|
| granulated sugar | 55.0 |
| glucose syrup | 43.5 |
| citric acid | 1.0 |
| flavoring substance | 0.2 |
| colorant | 0.2 |
| tamarind seed coat extract | 0.1. |

EXAMPLE 7

Juice:

By using the tamarind seed coat extract of Example 3, a juice of the following composition was produced. Neither the taste nor the color of the juice was affected by the tamarind seed coat extract added thereto.

| (Component) | (Content %) |
|---|---|
| Unshu mandarin juice (frozen and concentrated) | 5.0 |
| fructose/glucose liquid sugar | 11.0 |
| citric acid | 0.2 |
| L-ascorbic acid | 0.02 |
| flavoring substance | 0.2 |
| colorant | 0.1 |
| tamarind seed coat extract | 0.2 |
| water | 83.28. |

EXAMPLE 8

Chewing Gum:

By using the tamarind seed coat extract of Example 1, a chewing gum of the following composition was produced.

Neither the taste nor the color of the chewing gum was affected by the tamarind seed coat extract added thereto.

| (Component) | (Content %) |
|---|---|
| chewing gum base | 20.0 |
| sucrose | 55.0 |
| starch syrup | 20.0 |
| softener | 4.0 |
| flavoring substance | 0.85 |
| colorant | 0.1 |
| tamarind seed coat extract | 0.05. |

EXAMPLE 9

Chocolate:

By using the tamarind seed coat extract of Example 1, a chocolate of the following composition was produced. Neither the taste nor the color of the chocolate was affected by the tamarind seed coat extract added thereto.

| (Component) | (Content %) |
|---|---|
| chocolate | 45.0 |
| sucrose | 15.0 |
| cacao butter | 20.0 |
| whole fat powder milk | 19.9 |
| tamarind seed coat extract | 0.1. |

EXAMPLE 10

Cookie:

By using the tamarind seed coat extract of Example 3, a cookie of the following composition was produced. Neither the taste nor the color of the cookie was affected by the tamarind seed coat extract added thereto.

| (Component) | (Content %) |
|---|---|
| weak wheat flour | 31.77 |
| whole egg | 16.0 |
| margarine | 19.1 |
| refined white sugar | 25.5 |
| baking powder | 0.2 |
| water | 7.2 |
| laurel extract | 0.1 |
| tamarind seed coat extract | 0.13. |

EXAMPLE 11

Cookie:

By using the tamarind seed coat extract of Example 3, a cookie of the following composition was produced. Neither the taste nor the color of the cookie was affected by the tamarind seed coat extract added thereto.

| (Component) | (Content %) |
|---|---|
| weak wheat flour | 31.77 |
| whole egg | 16.0 |
| margarine | 19.12 |
| refined white sugar | 25.5 |
| baking powder | 0.2 |
| water | 7.2 |
| guava leaf extract | 0.08 |
| tamarind seed coat extract | 0.13. |

EXAMPLE 12

Gum:

By using the tamarind seed coat extract of Example 1, a gum of the following composition was produced. Neither the taste nor the color of the gum was affected by the tamarind seed coat extract added thereto.

| (Component) | (Content %) |
|---|---|
| gum base | 20.0 |
| calcium carbonate | 2.0 |
| wheat extract | 0.1 |
| lactose | 76.8 |
| flavoring substance | 1.0 |
| tamarind seed coat extract | 0.1. |

EXAMPLE 13

Gum:

By using the tamarind seed coat extract of Example 1, a gum of the following composition was produced. Neither the taste nor the color of the gum was affected by the tamarind seed coat extract added thereto.

| (Component) | (Content %) |
|---|---|
| gum base | 20.0 |
| calcium carbonate | 2.0 |
| oolong tea extract | 0.05 |
| lactose | 76.85 |
| flavoring substance | 1.0 |
| tamarind seed coat extract | 0.1. |

EXAMPLE 14

Dog Food:

By using the tamarind seed coat extract of Example 1, a dog food (dry type, moisture content: 10%) of the following composition was produced.

| (Component) | (Content) |
|---|---|
| meat meal | 38.0% (by wt.) |
| chicken extract | 5.0% |
| vegetable fat | 5.0% |
| carbohydrate | 37.0% |
| minerals | |
| calcium | 0.1% |
| phosphorus | 0.08% |
| sodium | 0.02% |
| potassium | 0.03% |
| iron | $5.0 \times 10^{-5}$% |
| vitamins | |
| vitamin A | 1000 IU |
| vitamin $B_1$ | $3.0 \times 10^{-4}$% |
| vitamin $B_2$ | $3.0 \times 10^{-4}$% |
| vitamin D | 100 IU |
| vitamin E | 10 IU |
| niacin | $5.0 \times 10^{-3}$% |
| pantothenic acid | $5.0 \times 10^{-3}$% |
| water | 10.0% |
| tamarind seed coat extract | 2.0%. |

EXAMPLE 15

Foaming Agent:

The tamarind seed coat extract obtained in Example 1 was mixed with the following components. Then the obtained mixture was processed into tablets by the direct powder compression method to thereby give a foaming agent.

| (Component) | (Content %) |
|---|---|
| granulated sugar | 40.0 |
| L-ascorbic acid | 11.0 |
| L-tartaric acid | 23.0 |
| sodium hydrogencarbonate | 22.0 |
| tamarind seed coat extract | 1.0 |
| cyanocobalamine | 0.3 |
| sodium citrate | 1.0 |
| sweetener | 1.0 |
| flavoring substance | 0.2 |
| colorant | 0.2 |
| sodium carbonate | 0.3. |

EXAMPLE 16

Beverage:

The tamarind seed coat extract obtained in Example 1 was mixed with the following components and water was added thereto to give a total volume of 1,000 ml. Thus a beverage in the form of sports drink was prepared.

| (Component) | (Content) |
|---|---|
| cations (mEq/l) | |
| $Na^+$ | 21.0 |
| $K^+$ | 5.0 |
| $Ca^{++}$ | 1.0 |
| $Mg^{++}$ | 0.5 |
| anions (mEq/l) | |
| $Cl^-$ | 16.5 |
| citrate$^{---}$ | 10.0 |
| lactate$^-$ | 1.0 |
| tamarind seed coat extract | 1.0 g |
| fructose | 20.0 g |
| glucose | 1.0 g |
| sucrose white sugar | 5.0 g. |

EXAMPLE 17

Beverage:

The tamarind seed coat extract obtained in Example 1 was dissolved in 1 l of water together with the following components to thereby give a beverage.

| (Component) | (Content) |
|---|---|
| tamarind seed coat extract | 0.5 g |
| xylooligosaccharide | 3.5 g |
| palatinose | 6.5 g |
| lactosucrose | 60.0 g |
| vitamin A | 11,500 IU |
| vitamin $B_1$ | 9.2 mg |
| vitamin $B_2$ | 9.2 mg |
| vitamin $B_6$ | 9.2 mg |
| vitamin $B_{12}$ | 27.7 μg |
| vitamin C | 3,464.4 mg |
| vitamin D | 9,923.6 IU |
| vitamin E | 69.3 IU |
| pantothenic acid | 46.2 mg |
| niacin | 92.4 mg |
| folic acid | 1,847.2 μg |
| biotin | 1,385.4 μg |
| vitamin K | 692.7 μg |
| choline | 1,154.5 mg |
| Ca | 2,309.0 mg |
| $PO_4$ | 2,309.0 mg |
| Mg | 923.6 mg |
| Na | 3,232.6 mg |
| K | 6,003.4 mg |
| Cl | 4,618.0 mg |
| Fe | 73.9 mg |
| Zn | 36.9 mg |
| Cu | 4.6 mg |
| Mn | 92.4 mg |
| I | 346.4 μg |
| flavoring substance | q.s. |

INDUSTRIAL APPLICABILITY

The antiobestic agent, carbohydrase inhibitor, blood sugar increase inhibitor, monosaccharide absorption inhibitor, cholic acid adsorptive excretion promoter, cholesterol lowering agent, blood triglyceride lowering agent and lipase inhibitor of the present invention have the antiobestic effect as well as the carbohydrase inhibitory effect, blood sugar increase inhibitory effect, monosaccharide absorption inhibitory effect, cholic acid adsorptive excretion promoting effect, cholesterol lowering effect, blood triglyceride lowering effect and lipase-inhibitory effect. Thus they are useful not only as antiobestic agents but also as antilipotrophic agents, antihyperlipemic agents, antiarteriosclerotic agents and antidiabetic agents. Tamarind seed coat extract or procyanidin extracted from seed coat of tamarind which has been employed as a food material, is highly safe and is free from any danger when taken into the human body.

The tamarind seed coat extract contains the active ingredient procyanidin in a very large amount. Therefore, it exhibits as such a potent antiobestic effect as well as the carbohydrase inhibitory effect, blood sugar increase inhibitory effect, monosaccharide absorption inhibitory effect, cholic acid adsorptive excretion promoting effect, cholesterol lowering effect, blood triglyceride lowering effect and lipase inhibitory effect without any further purification. Thus it can be easily produced at a low production cost. When it is added to foods or beverages, the antiobestic effect as well as the carbohydrase inhibitory effect, blood sugar increase inhibitory effect, monosaccharide absorption inhibitory effect, cholic acid adsorptive excretion promoting effect, cholesterol lowering effect, blood triglyceride lowering effect and lipase inhibitory effect can be achieved at a low addition level. Use of the antiobestic agent, carbohydrase inhibitor, blood sugar increase inhibitor, monosaccharide absorption inhibitor, cholic acid adsorptive excretion promoter, cholesterol lowering agent, blood triglyceride lowering agent and lipase inhibitor of the present invention makes it easy to produce foods or beverages having the carbohydrase inhibitory effect, blood sugar increase inhibitory effect, monosaccharide absorption inhibitory effect, cholic acid adsorptive excretion promoting effect, cholesterol lowering effect, blood triglyceride lowering effect and lipase inhibitory effect, which contributes to the relief or prevention of diabetes or obesity in our daily life. Accordingly, these products are useful as diet foods for healthy or obese people and, furthermore, foods or beverages for diabetics. Also, use of the antiobestic agent, carbohydrase inhibitor, blood sugar increase inhibitor, monosaccharide absorption inhibitor, cholic acid adsorptive excretion promoter, cholesterol lowering agent, blood triglyceride lowering agent and lipase inhibitor of the present invention makes it easy, compared with the conventional methods, to produce diet foods for animals such as pet animals, etc. and foods diabetic animals, which contributes to the relief or prevention of diabetes or obesity of mammals.

We claim:

1. A method of suppressing, relieving or preventing obesity, comprising the steps of administering to a mammal, including humans, in need of such treatment, a therapeutically effective amount of a food or beverage which includes a daily dose of from 1 to 300 mg/kg body weight of procyanidin as the active ingredient.

2. A method of suppressing, relieving or preventing obesity, comprising the steps of administering to a mammal, including humans, in need of such treatment, a therapeutically effective amount of a food or beverage which includes a daily dose of from 1 to 300 mg/kg body weight of procyanidin as the active ingredient which has a carbohydrase inhibitory effect.

3. A method of suppressing, relieving or preventing obesity, comprising the steps of administering to a mammal, including humans, in need of such treatment, a therapeutically effective amount of a food or beverage which includes a daily dose of from 1 to 300 mg/kg body weight of procyanidin as the active ingredient which has a blood sugar increase inhibitory effect.

4. A method of suppressing, relieving or preventing obesity, comprising the steps of administering to a mammal, including humans, in need of such treatment, a therapeutically effective amount of a food or beverage which includes a daily dose of from 1 to 300 mg/kq body weight of procyanidin as the active ingredient which has a monosaccharide inhibitory effect.

5. A method of suppressing, relieving or preventing obesity, comprising the steps of administering to a mammal, including humans, in need of such treatment, a therapeutically effective amount of a food or beverage which includes a daily dose of from 1 to 300 mg/kg body weight of procyanidin as the active ingredient which has a cholic acid adsorptive excretion promoting effect.

6. A method of suppressing, relieving or preventing obesity, comprising the steps of administering to a mammal, including humans, in need of such treatment, a therapeutically effective amount of a food or beverage which includes a daily dose of from 1 to 300 mg/kg body weight of procyanidin as the active ingredient which has a cholesterol lowering effect.

7. A method of suppressing, relieving or preventing obesity, comprising the steps of administering to a mammal, including humans, in need of such treatment, a therapeutically effective amount of a food or beverage which includes a daily dose of from 1 to 300 mg/kg body weight of procyanidin as the active ingredient which has a blood triglyceride lowering effect.

8. A method of suppressing, relieving or preventing obesity, comprising the steps of administering to a mammal, including humans, in need of such treatment, a therapeutically effective amount of a food or beverage which includes a daily dose of from 1 to 300 mg/kg body weight of procyanidin as the active ingredient which has a lipase inhibitory effect.

9. The method as claimed in any of claims 1 to 8 wherein said procyanidin is one obtained from extract of tamarind seed coat.

10. The method as claimed in claim 9 wherein said procyanidin is one extracted with one or more solvents selected from among water, methanol, ethanol, isopropanol, butanol, propylene glycol, butylene glycol, glycerol, acetone, ethyl acetate and methyl ethyl ketone.

11. A method for producing food which suppresses, relieves or prevents obesity comprising the step of adding procyanidin in a daily dose of from 1 to 300 mg/kq body weight to the food.

12. A method for producing animal feed which suppresses, relieves or prevents obesity comprising the step of adding procyanidin in a daily dose of from 1 to 300 mg/kg body weight to the animal feed.

* * * * *